United States Patent
Cameron et al.

(10) Patent No.: US 9,739,892 B2
(45) Date of Patent: Aug. 22, 2017

(54) FAST, HIGH-RATE, POSITION-SENSITIVE ABSOLUTE DOSIMETER FOR ION BEAM THERAPY

(71) Applicants: John M. Cameron, Bloomington, IN (US); Alexander V. Klyachko, Bloomington, IN (US); Keith A. Solberg, Bloomington, IN (US); Steven E. Vigdor, Bloomington, IN (US)

(72) Inventors: John M. Cameron, Bloomington, IN (US); Alexander V. Klyachko, Bloomington, IN (US); Keith A. Solberg, Bloomington, IN (US); Steven E. Vigdor, Bloomington, IN (US)

(73) Assignee: Phenix Medical LLC, Bloomington, IN (US)

( * ) Notice: Subject to any disclaimer, the term of this patent is extended or adjusted under 35 U.S.C. 154(b) by 178 days.

(21) Appl. No.: 14/248,499

(22) Filed: Apr. 9, 2014

(65) Prior Publication Data
US 2015/0293235 A1 Oct. 15, 2015

(51) Int. Cl.
*G01T 1/02* (2006.01)
*A61N 5/10* (2006.01)

(52) U.S. Cl.
CPC .......... *G01T 1/023* (2013.01); *A61N 5/1071* (2013.01); *A61N 5/1043* (2013.01); *A61N 2005/1087* (2013.01)

(58) Field of Classification Search
CPC .. G01T 1/20; G01T 1/023; G21K 5/10; A61N 5/1048; A61N 5/1077; A61N 2005/1087; H01J 2237/2443
See application file for complete search history.

(56) References Cited

U.S. PATENT DOCUMENTS

| | | |
|---|---|---|
| 3,805,076 A | 4/1974 | Carroll, Jr. |
| 4,131,799 A | 12/1978 | Stieber |

(Continued)

FOREIGN PATENT DOCUMENTS

| | | |
|---|---|---|
| CA | 2 275 159 A1 | 4/1999 |
| EP | 0 616 722 B1 | 12/1996 |

(Continued)

OTHER PUBLICATIONS

U. Schneider, S. Agosteo, E. Pedroni, J. Besserer, *Secondary Neutron Dose During Proton Therapy Using Spot Scanning*, Int. J. Radiat. Oncol. Biol. Phys. 53, 244 (2002).

T. Furukawa, T. Inaniwa, S. Sato, T. Shirai, S. Mori, E. Takeshita, et al., *Moving target irradiation with fast rescanning and gating in particle therapy*, Med. Phys. 37, 4874 (2010).

(Continued)

*Primary Examiner* — David Porta
*Assistant Examiner* — Faye Boosalis
(74) *Attorney, Agent, or Firm* — Reinhart Boerner Van Deuren P.C.

(57) ABSTRACT

A gas scintillation detector is designed to provide in-beam absolute dose monitoring for ion beam radiotherapy treatments employing spot or raster beam scanning, especially with microsecond-scale beam pulses. Detection of prompt primary scintillation light emitted by gas molecules excited by beam passage provides electronic signals that can be processed to yield output data proportional to delivered dose up to high dose rates, and that appear quickly enough to provide feedback to influence real-time beam intensity adjustments for subsequent steps in the beam scan. When the scintillation light is collected in multiple photo-detectors, the invention is furthermore capable of measuring spot beam position with spatial resolutions of order one millimeter.

31 Claims, 4 Drawing Sheets

(56) References Cited

U.S. PATENT DOCUMENTS

| | | | |
|---|---|---|---|
| 4,803,368 A | | 2/1989 | Barthelmes |
| 4,931,653 A | * | 6/1990 | Hamm ................. G01T 1/2935 250/361 R |
| 5,517,030 A | | 5/1996 | Nabais Conde et al. |
| 6,627,897 B1 | * | 9/2003 | Francke ................. G01T 1/185 250/374 |
| 6,787,771 B2 | * | 9/2004 | Bashkirov ............... H01J 49/40 250/287 |
| 7,663,081 B2 | | 2/2010 | Hahn et al. |
| 7,675,040 B2 | | 3/2010 | Menge et al. |
| 8,363,775 B1 | | 1/2013 | Guardala et al. |
| 8,476,595 B2 | | 7/2013 | McKinsey et al. |
| 8,541,762 B2 | | 9/2013 | Claereboudt et al. |
| 8,586,941 B2 | | 11/2013 | Harada et al. |
| 8,975,600 B2 | * | 3/2015 | Balakin ...................... 250/492.1 |
| 2002/0175291 A1 | * | 11/2002 | Reeder et al. ................. 250/369 |
| 2007/0171015 A1 | | 7/2007 | Antaya |
| 2010/0012859 A1 | | 1/2010 | Claereboudt |
| 2012/0080618 A1 | * | 4/2012 | Clayton et al. ............ 250/492.3 |
| 2012/0104270 A1 | | 5/2012 | Marchand et al. |
| 2013/0287170 A1 | * | 10/2013 | Ebstein ................. G01N 23/04 378/62 |

FOREIGN PATENT DOCUMENTS

| | | |
|---|---|---|
| EP | 0 838 844 A2 | 4/1998 |
| EP | 1 315 002 A1 | 5/2003 |
| WO | WO 96/24072 A1 | 8/1996 |
| WO | WO 02/101414 A1 | 12/2002 |
| WO | WO 03/021276 A1 | 3/2003 |
| WO | WO 2006/005059 A2 | 1/2006 |
| WO | WO 2007/121876 A2 | 11/2007 |
| WO | WO 2008/119777 A1 | 10/2008 |
| WO | WO 2010/095967 A1 | 8/2010 |
| WO | WO 2013/060745 A1 | 5/2013 |
| WO | WO 2013/138088 A2 | 9/2013 |
| WO | WO 2013/149945 A1 | 10/2013 |

OTHER PUBLICATIONS

S. Zenklusen, E. Pedroni and D. Meer, *A Study on Repainting Strategies for Treating Moderately Moving Targets with Proton Pencil Beam Scanning at the New Gantry 2 at PSI*, Phys. Med. Biol. 55, 5103 (2010).

A.J. Lomax, *An Overview of Compensated and Intensity-Modulated Proton Therapy*, AAPM Summer School, 2003 (http://www.aapm.org/meetings/03SS/Presentations/Lomax.pdf).

* cited by examiner

FAST, HIGH-RATE, POSITION-SENSITIVE ABSOLUTE DOSIMETER FOR ION BEAM THERAPY

FIELD OF THE INVENTION

This invention generally relates to systems and methods in the technical field of dosimetry for radiotherapy. More particularly, the present invention is in the technical field of in-beam dosimetry for ion beam therapy.

BACKGROUND OF THE INVENTION

Cancer therapy via irradiation with energetic beams of protons or heavier ions has intrinsic physical advantages over the more widespread radiotherapy modalities based on X-rays. The ion beams deposit their energy much more selectively, primarily within a small volume (referred to as the Bragg peak) near the endpoint of the beam particle's path within the patient. This permits high radiation doses to be delivered to a tumor, while minimizing the dose to surrounding healthy tissue, and especially to sensitive organs that may be adjacent to the tumor volume. This physical advantage greatly reduces long- and short-term toxicity side effects of the radiation treatment.

In order to take full advantage of the ion beam benefits, a new generation of ion beam therapy technology is being developed, to make the treatment faster, more precise, simpler, cheaper and requiring much smaller footprints, so that it becomes economically more competitive with X-ray therapy. These new ion beam therapy facilities require advanced technical developments in the accelerators that produce the beams, in the gantry systems that deliver the beams to a patient from multiple angles, in the system that scans a beam of small cross-sectional area (a so-called "pencil beam"), and of adjustable energy and intensity, over the tumor volume and in the detector systems that carefully monitor and provide feedback on the delivered dose.

A central aspect of these new facilities is Intensity Modulation, typically provided by the use of so-called "spot beam scanning" (SBS). In this approach, an intense beam of small (sub-centimeter) diameter is used to deposit energy in a very short (no more than several milliseconds) time interval, primarily in a very small volume ("voxel") near the back (distal) edge of a tumor. Electromagnets are then used to move the beam transversely in 2 dimensions to irradiate a neighboring voxel. With many more such steps, the entire lateral dimension of the deepest part of the tumor is irradiated. Then the beam energy is reduced and a similar transverse scan, though generally of different lateral extent, deposits energy primarily in a tumor slice slightly less deep within the patient. This sequence is repeated until the entire tumorous volume is "painted" with radiation. The beam intensity can be varied with each voxel in the entire scanning sequence to arrange for a radiation dose that conforms as closely as possible to the (arbitrary-shaped) tumor volume.

The SBS approach is more cost-effective and potentially more precise than conventional passive scattering treatments, with which it is compared schematically in FIGS. 1 and 2. But SBS is also more sensitive to organ motion. The interplay between the scanned beam frequency and the target motion frequency can result in localized under-dosage in parts of the target volume and over-dosage in other parts, an effect that has been seen in both simulations and experimental data. This sensitivity can be ameliorated in an alternative to the "pointillist" SBS approach, by scanning the ion beam continuously at a rate of at least a few cm/millisecond over a raster pattern in two dimensions, while varying the beam intensity continuously during the scan. The latter Raster Beam Scanning (RBS) approach can decrease the painting time of the tumor within a given depth layer by an order of magnitude compared to conventional SBS, so that multiple repaints of the depth layer can be performed within a time interval much shorter than typical organ motion periods in the patient's body. In either intensity modulation approach, SBS or RBS, the angle of beam entry can be changed by rotating the gantry for subsequent scans, to avoid radiation to critical organs and to spread any undesired radiation of healthy tissue outside the tumor over a larger volume.

Clinical application of pencil beam scanning in either of the above approaches requires accurate (to the 2% level) monitoring of the radiation dose delivered to each voxel, with the possibility of rapid feedback to the control system to alter the irradiation plan for subsequent voxels or subsequent repaints or subsequent tumor layers. The ionization chambers in current widespread usage as ion beam dosimeters are not well suited to this purpose. They have shortcomings associated with non-linear response at the high beam fluxes (number of incident particles per second per square centimeter) foreseen, they do not provide dose measurements on the needed sub-millisecond time scales, and when they are sensitive to beam position, their measurements typically provide marginal spatial resolution for determining definitively that the beam has indeed moved from voxel to voxel or for pinpointing locations where beam may have been off during a raster scan.

The non-linearity is especially problematic for next-generation ion beam therapy facilities that will utilize superconducting synchrocyclotrons or alternative accelerators that deliver pulsed beams. These accelerators deliver the beam for each voxel in beam pulses that last typically no longer than ten microseconds, while succeeding pulses are separated by about 1 millisecond, thus amplifying the instantaneous beam flux to which the dosimeter is exposed by a factor of 100 or more. The non-linearity is further exacerbated for heavier ion beams, which yield higher ionization density within the ionization chambers. Furthermore, the relatively slow response time and marginal spatial resolution provided by the ionization chambers limits their ability to provide rapid feedback to the control system when hardware or software problems may produce unexpected dose delivery to a given voxel, or may interrupt a treatment that needs to be continued from the last irradiated voxel after the system is successfully restored.

Alternative dosimetry systems currently employed in ion beam therapy have similar limitations. Integrating detectors such as radiochromic films and alanine detectors have limited applications since they are not real-time devices. Scintillator screens viewed by CCD cameras represent the most popular type of real-time quality assurance (QA) detectors, typified by the Lynx PT detector commercially available from vendor, IBA. Although the scintillating screen provides excellent spatial resolution to identify beam position, its fundamental drawback is that the detector response is not linear with dose when the beam stopping power approaches its maximum value.

In radiochromic films, this non-linearity leads to underestimation of dose of up to 20% at the peak of the Bragg curve. In scintillator screens, as much as 20% quenching of the light output in a proton beam, 30% in an $\alpha$-particle beam and 43% in a carbon beam has been observed at high ionization densities (i.e. at the Bragg peak). Furthermore, for on-line monitoring applications with scanning beams, the limited processing speed of modern CCD cameras (<40 frames per second) is too slow to match the requirements of sub-millisecond feedback. Gas Electron Multiplier (GEM) chambers with electronic readout are often used in nuclear and particle physics experiments to provide fast detectors with excellent spatial resolution, and hence, they have promise for in-beam dosimetry. However, they are known to provide output signal amplitudes that vary significantly with position, dose rate and dose history, making them inappropriate for absolute dose determination. Scintillating GEM detectors with optical readout have been proposed for quality assurance on scanning ion beam treatment plans, but again with CCD readout making them too slow for real-time feedback to the beam scanning control system.

Intensity-modulated ion beam therapy, delivered via either spot or raster beam scanning, thus requires cost-effective dosimeters that are as accurate as ionization chambers at moderate dose rates, while providing improved linearity at high dose rates, faster response time, and higher spatial resolution, still with an overall signal strength that varies negligibly when a fixed-intensity beam spot moves across the detectors.

Embodiments of the present invention provide such a single detector with the capability to satisfy all of these above-referenced requirements simultaneously, representing a much more cost-effective approach than would be obtained by combining multiple different detectors of the above-mentioned types, to overcome their individual limitations. These and other advantages of the invention, as well as additional inventive features, will be apparent from the description of the invention provided herein.

BRIEF SUMMARY OF THE INVENTION

In one aspect, embodiments of the invention provide a gas scintillation detector (GSD) to provide absolute measurement of delivered radiation doses and their spatial distribution for spot or raster beam scanning approaches to Intensity-Modulated ion beam radiotherapy. The GSD is characterized by high linearity, high accuracy, and fast response. When the beam is to be scanned across a field of large (typically 10 centimeters or more) lateral dimension, readout of the GSD with multiple photo-detectors can provide a summed signal with excellent spatial uniformity of response to the absolute dose, plus difference signals sensitive to beam position with spatial resolution well suited to beam scanning modalities.

The GSD exploits the light emitted by gas molecules, typically within 100 nanoseconds after they have been excited by ion beam passage, when they return to their original lowest energy state. The short time scale characteristic of this physical process makes it much better suited to spot or raster beam scanning, especially with pulsed-beam accelerators, than ionization chambers, which rely on the slower process of collecting positive ions created by the interaction of the passing beam particles with atomic electrons in the chamber gas. In particular, the performance of ionization chambers is significantly compromised at high dose rates by the recombination of positive and negative ions within the chamber gas, which occurs typically within milliseconds. The promptness of the scintillation light makes the GSD insensitive to such recombination effects.

The scintillation light from the GSD can be converted to fast electronic signals using commercially available photomultiplier tubes (PMTs) or equivalent solid-state devices, such as avalanche photodiodes (APDs), optically coupled to the GSD volume. The APDs may eventually be preferable for GSD installation near the exit of an ion beam gantry, where fringe magnetic fields may affect the operation of PMTs. For either readout approach, an electronic signal can be generated, whose amplitude measures the delivered dose, and which is available sufficiently promptly for feedback to influence the real-time adjustment of beam intensity for subsequent steps in a beam scan.

To accommodate the largest tumors that would be subjected to ion beam therapy, it is desirable to utilize multiple photo-detectors to convert the light, comprising pairs located at opposite sides of the gas volume. Then the summed signal from all photo-detectors will measure the absolute dose, while the differences in signals between opposite photo-detectors will be used to measure the two-dimensional transverse location at which the pencil beam crosses the detector. The stability over time of the photo-detectors' response and gain, hence the reliability of the absolute dose and position measurements, can be monitored periodically by injecting light into the gas volume from embedded light-pulsers. The GSD would then single-handedly provide a complete record of the irradiation treatment, including the dose delivered and the lateral position at which it was delivered for every beam pulse used in the treatment. Even if the beam is not pulsed, and is scanned continuously, the GSD is capable of recording this information for a succession of short (~100 microseconds or less) time intervals during which the beam does not move by more than a few millimeters.

Noble gases represent an attractive choice for the detection medium. Noble gas scintillation detectors have been developed and utilized previously, but for very different applications, usually involving measurement of the energy deposited by single passing particles. In nearly all of these previous applications, special pains were taken to compensate for the usual drawback of gaseous scintillators, namely, that their low density leads to much lower light yield than in liquid or solid scintillators. Thus, most of the previous applications utilize the gas at high pressures, or even in combination with the same material in liquid form.

These previous applications often involve applied voltages to accelerate electrons liberated from ionized gas atoms, so that subsequent interactions of these electrons with gas atoms may produce secondary (slower) scintillation light, in addition to the primary light arising from the interactions of the primary incident particles. They also typically involve highly reflective gas cell walls to increase light collection efficiency. These features would have undesirable implications in the present application, where exposure to a primary charged-particle beam generating abundant light allows scintillator operation in a very different regime: even a single beam pulse will generally produce hundreds of millions of photons. In this case, the gas pressure can be kept moderate, accelerating voltages can be avoided, and gas cell walls can be made non-reflective. These operational characteristics allow us to enhance the detector's response speed, linearity, spatial resolution and resistance to performance changes introduced by possible gas impurities.

In another aspect, embodiments of the invention provide a radiation detector for absolute monitoring of radiation doses delivered by an ion beam. The radiation detector includes a gas-tight housing with windows in the beam path, a gaseous medium, or scintillating gas, within the housing, wherein scintillation light is emitted by the gaseous medium after it is traversed by the ion beam, and one or more photo-detectors located around the gas-tight housing and optically coupled to the gas volume. The one or more photo-detectors are configured to convert collected scintillation light into electric current. The radiation detector may also comprise readout electronics and a processor configured to generate a digitized electronic signal whose magnitude is proportional to the total amount of energy deposited by the ion beam in the gaseous volume. Embodiments of the radiation detector further include a photo-detector base for each of the one or more photo-detectors, wherein the photo-detector base couples its respective photo-detector to the readout electronics and the processor. In a particular embodiment, the scintillation light emitted by the gaseous medium has a duration of less than 100 nanoseconds.

In certain embodiments of the invention, the ion beam generates output data from said processor, the output data being indicative of a dose delivered by the ion beam to which the radiation detector was exposed, the output data being accurate to within 2% of the actual dose. In a further embodiment, the output data generated by the processor comprises an electronic signal whose magnitude is directly proportional to the dose delivered by the ion beam. Moreover, the proportionality of the output data to the dose may be maintained when the dose is delivered within ion beam pulses as short as one microsecond at instantaneous beam currents of up to 10 microamperes.

In at least one embodiment, the output data of said processor are available on sub-millisecond time scales, to provide feedback for real-time adjustment of ion beam intensity for subsequent steps in dose delivery. The processor may be configured to allow archiving of the digitized signals from each of the one or more photo-detectors on a beam-pulse-by-beam-pulse basis, or on a sampling-interval-by-sampling-interval basis, to provide a complete record of the dose delivered. The processor may be further configured to allow archiving of the digitized signals from each of the one or more photo-detectors to provide a complete record of the position at which the dose was delivered.

The radiation detector may also include readout electronics coupled to the processor and configured to integrate over time and digitize the electric current output by the one or more photo-detectors. The readout electronics may be configured to be triggered by external electronic input signals to integrate photo-detector output electric currents only during time intervals when the ion beam is incident on the detector or during such other sampling time periods as the user may desire.

Embodiments of the radiation detector further include a plurality of photo-detectors located around the gas-tight housing, wherein the processor determines the difference between signals from oppositely-situated photo-detectors of the plurality of photo-detectors, divided by the sum of said signals, to provide output data sensitive to a distance of the ion beam from each of the oppositely-situated photo-detectors. The processor may be configured to determine ion beam position with spatial resolution sufficient to detect beam motion from one beam pulse to the next. In some embodiments, the gas-tight housing includes mounts for two pairs of oppositely-situated photo-detectors such that each photo-detector is oriented at 90 degrees from an adjacent photo-detector, wherein the processor is configured to determine two-dimensional movement of the ion beam from one beam pulse to the next. In particular embodiments, the processor is configured to determine ion beam lateral position with spatial resolution of two millimeters or better.

The gas tight housing may include ion beam entry and exit windows sized to accommodate the movement of the ion beam in two dimensions. The one or more photo-detectors may comprise a plurality of optical fibers or strip light guides to transport light to multi-channel photo-detectors. In a particular embodiment, the multi-channel photo-detectors comprise multi-anode photomultiplier tubes.

Embodiments of the radiation detector may further include wavelength-shifting optical fibers that shift the light emitted by the gaseous medium to improve overlap with a spectral response of the one or more photo-detectors. The gaseous medium could be xenon, for example, or a mixture of 95% argon and 5% carbon tetrafluoride. Further, the gaseous medium may be maintained at a pressure of one atmosphere.

Embodiments of the radiation detector further include one or more light-pulsers, which emit light at wavelengths within the spectral response region of the one or more photo-detectors, and are triggered by external electronic signals to provide periodic calibration of a photo-detector spectral response to reproducible amounts of light injected at known locations. The one or more light-pulsers may include one or more light-emitting diodes (LEDs). In certain embodiments, the one or more light-pulsers are embedded inside of the gas-tight housing.

In a particular embodiment, the entire detector is mounted to a rotatable beam gantry, without interfering with dose delivery apparatus or patient tables. In a certain embodiment, scintillation light is emitted by the gaseous medium after it is traversed by the ion beam. Further, the one or more photo-detectors may include one or more photomultiplier tubes, or one or more large-area avalanche photodiodes. Embodiments of the radiation detector further include transparent windows to optically couple the gaseous medium and the one or more photo-detectors. The windows may include an anti-reflection coating on the sides exposed to the gas, optimized to minimize reflections for wavelengths of peak optical emission from the scintillating gaseous medium. In some embodiments, the transparent window material may be quartz or fused silica to optimize light transmission in the ultraviolet and vacuum ultraviolet regions of the light spectrum.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Embodiments of the present invention are generally described herein with respect to the benefits and advantages derived from its application in the medical field. Embodiments of the invention are especially well-suited for the scanning of intense accelerator beams of small cross-sectional area (so-called "pencil beams"), and of adjustable energy and intensity, to conformally irradiate the full volume of an arbitrary-shaped target tumor while providing minimal dose to surrounding healthy tissue. However, one of ordinary skill in the art would also recognize that a dosimeter, which satisfies the clinical demands described above, is also likely in other embodiments to find application as a diagnostic tool for various non-therapeutic uses of pulsed ion beam bombardment, e.g., to modify material properties via ion implantation or in studies of novel methods to produce such beams, e.g., by the interaction of intense laser pulses with thin film or gas jet targets.

Figure 1:
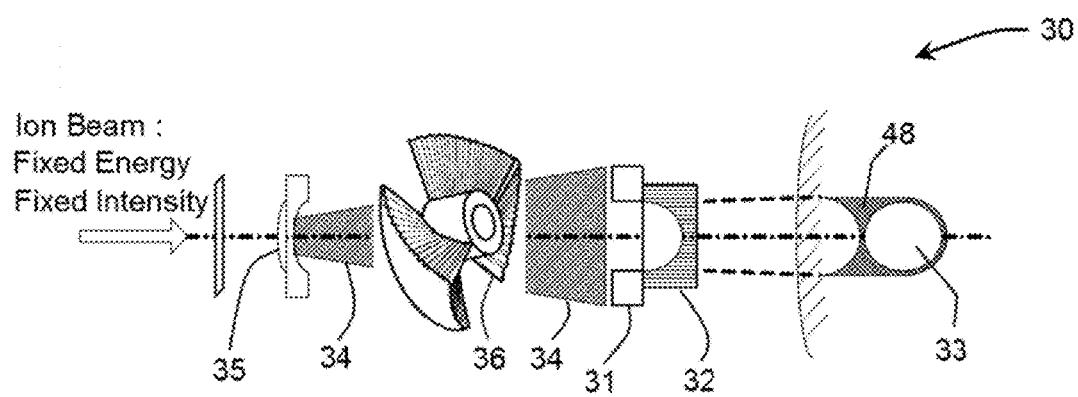
FIG. 1 is a schematic plan view of a conventional passive scattering system for delivery of an ion beam of fixed energy and intensity to irradiate a tumor with the aid of patient-specific apertures and compensators.
Figure 2:
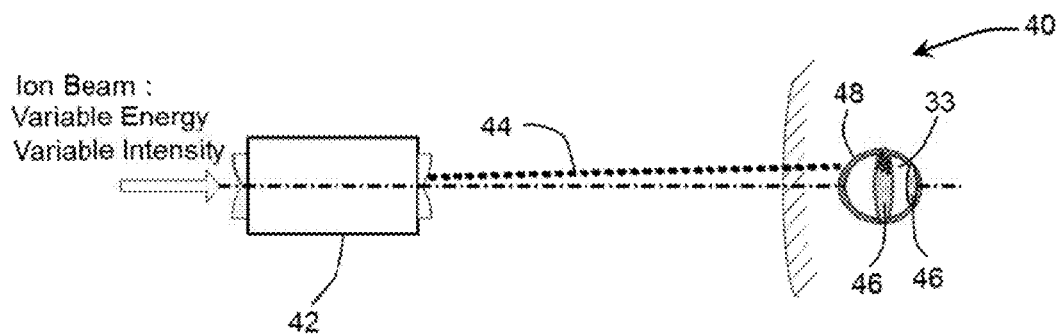
FIG. 2 is a schematic plan view of a pencil beam scanning system for delivery of an ion beam of variable energy and intensity to irradiate a tumor.

FIG. 1 shows a schematic plan view of a conventional fixed-energy, fixed-intensity passive scattering system 30 for ion beam therapy delivery to a target volume, or tumor 33, using patient-specific apertures 31 and compensators 32 to form the desired radiation field from the broad beam 34 produced via scattering foils 35 and a range modulator 36. FIG. 2 shows a schematic plan view of a system 40 for delivery of variable-energy, intensity-modulated ion beam therapy, using a scanning system 42 to scan a pencil beam 44 across depth layers 46 of a tumor. Comparison of the shaded areas 48 in FIGS. 1 and 2, schematically indicating dose distributions outside the tumor volume, illustrate how pencil beam scanning can lead to reduced irradiation of healthy tissue adjacent to the tumor.

Figure 3:
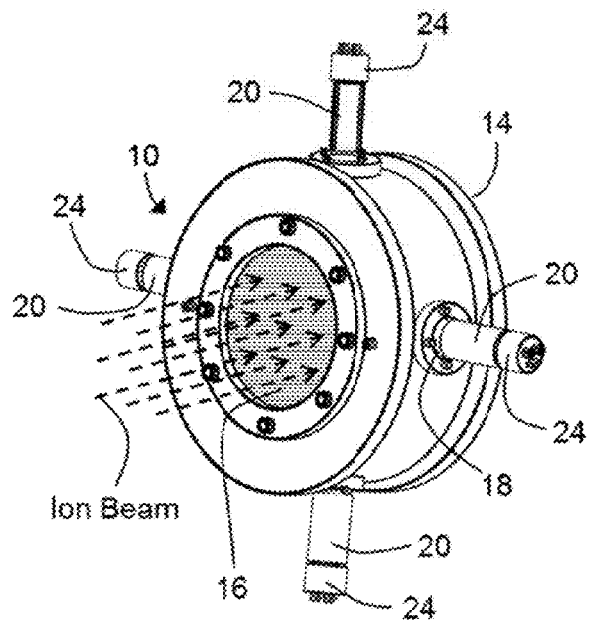
FIG. 3 provides a perspective view of a gas scintillation detector, in accordance with an embodiment of the invention.
Figure 4:
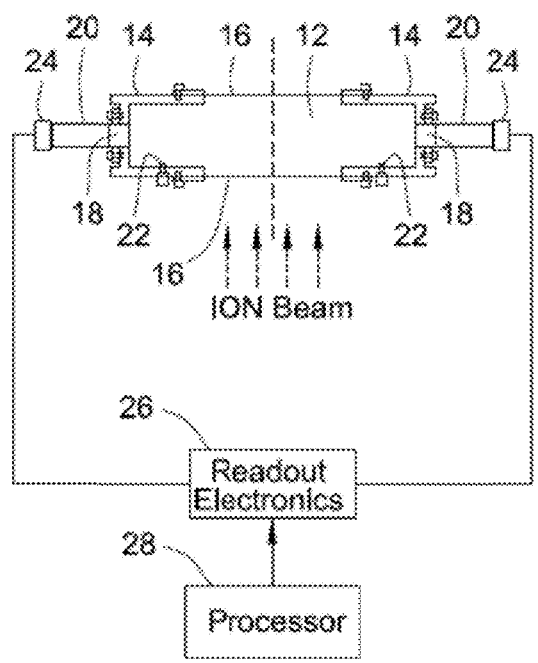
FIG. 4 provides a cross-sectional view of a gas scintillation detector, in accordance with an embodiment of the invention.

FIG. 3 shows a perspective view of a gas scintillation detector 10, according to an embodiment of the invention, while FIG. 4 shows a cross-sectional view of the gas scintillation detector 10 of FIG. 3. In the configuration of FIGS. 3 and 4, the gas scintillation detector has four photo-detectors 20 for light collection. In this particular example, the photo-detectors 20 are photomultiplier tubes. In an actual installation, the photomultiplier tubes 20 would be surrounded by thin cylindrical shields (not shown) to keep out light and ambient magnetic fields.

As can be seen in FIGS. 3 and 4 there is shown an exemplary embodiment, in which the gas scintillation detector 10 comprises a gas volume 12 contained in a detector housing 14 with thin beam entry and exit windows 16 and with transparent windows 18, such as quartz windows 18 for example, to allow optical coupling of the gas volume to photomultiplier tubes 20. LEDs 22 (or alternative light-pulsing devices) are embedded in the detector housing walls to produce light pulses used for calibration of the photomultiplier tube responses. Control voltage input to, and signal output from, the photomultiplier tubes 20 are supplied via photo-detector bases 24. The photo-detector bases 24 also connect the photomultiplier tubes 20 (or other suitable photo-detectors) to readout electronics modules 26, which are, in turn, connected to a processor 28.

In more detail, still referring to the invention of FIGS. 3 and 4, the passage of beam particles through the gas volume 12 excites gas molecules, which subsequently de-excite with the emission of prompt scintillation light. Some fraction of the emitted scintillation light is collected by the photomultiplier tubes 20, which convert the collected photons to electrons (referred to as photoelectrons), and thence, to amplified electric currents. The output currents are transmitted to the readout electronics modules 26 via the photo-detector bases 24. The readout electronics 26 serve to integrate the output currents within a time interval matched to the incident beam pulse width, and subsequently to digitize the integrated currents. The digitized integrated data output from the readout electronics 26 is then transmitted to the processor 28 to form appropriate sums, differences and ratios of the data from individual photo-detectors 20, which yield final data proportional to the number of beam protons within the pulse that passed through the detector 10, and to the two-dimensional position at which the centroid of the beam pulse passed. The processor 28 can furthermore apply stored calibration information to provide the user with measurements of absolute radiation dose and beam position in the desired units, and can archive all of these output data for each beam pulse for subsequent retrieval.

In further detail, still referring to the invention of FIGS. 3 and 4, the detector 10 can be placed in-beam in front of the patient to be irradiated without significant effect on the beam properties, because the energy lost by beam particles and their multiple scattering within the detector 10 are minimized by the use of thin entry and exit windows 16 and a gaseous detector material 12 at moderate pressure. The detector housing 14 should be vacuum-tight to prevent gas leakage, and must provide housing for entry and exit windows 16 that are thick enough to withstand the gas pressure and possible evacuation of the gas volume 12, but thin enough to provide minimal disruption of the beam properties. The lateral extent of the entry and exit windows 16 must be large enough to encompass the full transverse extent of planned beam scans. Since beam monitoring detectors are usually placed halfway between the scanning magnet(s) and the isocenter where the target tumor will be located, windows 16 of about 9 cm radius would be sufficient for covering the largest radiation fields (usually no more than 25×25 cm$^2$ at the patient location) used in clinical practice. The radius of the cylindrical detector housing 14 should be significantly greater than the radius of the windows, in order to limit the sensitivity to beam position of the dose measurement output signal generated from the summed output signals of the photomultipliers 20.

In further detail, still referring to the invention of FIGS. 3 and 4, the gas chosen and the pressure and thickness of the gas volume 12 must be suitable to generate an adequate amount of scintillation light, while providing minimal disruption of the beam properties. Since in some embodiments the emission spectrum for the scintillation light may include significant portions in the ultraviolet, the quartz windows 18 may have good UV transparency. The chosen photomultiplier tubes 20 should have good quantum efficiency for converting photons within the frequency range emitted by the gas into electrons, and should be coupled to photodetector bases 24 that provide highly linear signal response over a broad range of input light intensity.

For operation in the vicinity of an ion beam delivery gantry, the photomultiplier tubes 20 may need to be carefully shielded from ambient magnetic fields, in order to avoid gain changes when magnets are adjusted during beam scans. For use in a clinical setting, 4 PMTs viewing the sensitive volume of the detector, with signal processing electronics, will be sufficient to ensure light collection uniformity at the 2% level or better as the beam is scanned across the transverse acceptance of the entry and exit windows 16. Comparison of the signal magnitudes or amplitudes generated in the different PMTs can then provide a determination of the location of the traversing beam with spatial resolution relevant to spot or raster beam scanning We furthermore envision that the LEDs 22 will be triggered periodically to inject known amounts of light, at wavelengths within the PMT response spectrum, and at known locations for the purpose of monitoring reproducibility of the PMT responses.

A prototype embodiment of the invention in FIGS. 3 and 4 has already been subjected to in-beam performance tests. In construction detail, this particular embodiment consisted of a stainless steel vacuum-tight housing 14 with fused silica UV-transparent windows 18 on two sides and 38-μm-thick stainless steel entrance and exit windows 16 in the beam path. Xenon was chosen as the first gas to be tested because its diatomic molecules (dimers) are excited in interactions accounting for about 20% of the energy loss experienced by passing protons, and they de-excite in less than 100 nanoseconds via the process $Xe_2 \rightarrow 2Xe + photon$, emitting photons in the vacuum ultraviolet (VUV) range of the spectrum. The fast primary scintillation light from this dimer excitation is relatively insensitive to the presence of contaminant gases, and produces orders of magnitude more photons per amount of energy deposited than likely contaminant gases, such as nitrogen. In the prototype embodiment, the pressure within the gas scintillator volume 12 was maintained at one atmosphere.

Alternative embodiments of the detector may involve different gases at different pressures. One possibility is a gas mixture of argon (95%) and carbon tetrafluoride (5%). This mixture is considered one of the brightest scintillating gases, although its emission spectrum is shifted towards visible and near infrared wavelengths compared to that of Xe. In alternative embodiments, the gas handling system may also include a recirculating gas purification system, in case the long-term stable performance of the dosimeter may be compromised by small gas impurities.

Alternative embodiments of the detector may also include different types of photo-detector for converting light to electric currents and/or different geometrical arrangements of the photo-detectors. For example, the light collection efficiency and the position resolution may be enhanced by use of many optical fibers or strip light guides to transport light, and possibly to shift its wavelength, to multi-channel photo-detectors, such as multi-anode photomultiplier tubes. As the technology for producing large-area avalanche photodiodes (LAAPDs) improves, LAAPDs may present an interesting alternative to PMTs for GSD readout. The LAAPD advantages include mechanical robustness, insensitivity to ambient magnetic fields, and excellent quantum efficiency throughout a broad range of the light spectrum, from VUV through visible and into the near infrared. However, the disadvantages of currently available LAAPDs for the present application are considerable: much lower gain than PMTs, higher noise, higher gain sensitivity to ambient temperature and some non-linearity of response at high currents.

Figure 6:
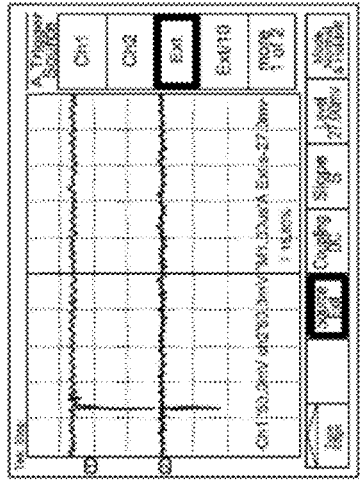
FIG. 6 is a graphical illustration of recorded oscilloscope signals, at a second time scale, for the pulses generated in two photo-detectors of the gas scintillation detector, according to an embodiment of the invention.
Figure 5:
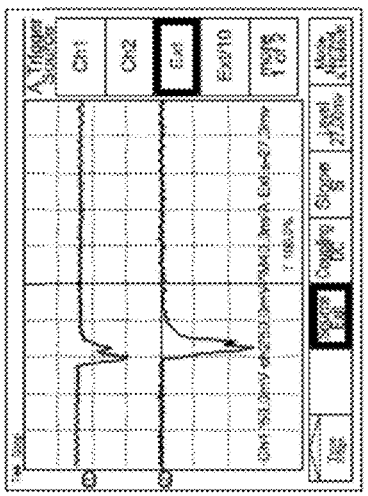
FIG. 5 is a graphical illustration of recorded oscilloscope signals, at a first time scale, for the pulses generated in two photo-detectors of the gas scintillation detector, according to an embodiment of the invention.

FIGS. 5 and 6 show recorded oscilloscope signals for the pulses generated in the two photomultiplier tubes on a prototype xenon-filled GSD by traversal of single protons of about 100 MeV. The oscilloscope traces on two different time scales—(a) 40 nanoseconds per major division (FIG. 5), and (b) 1.0 microsecond per major division (FIG. 6)—show that the response is faster than that of conventional detectors and free of slow secondary pulses.

With respect to FIGS. 5 and 6, the beam tests of the prototype embodiment demonstrate the excellent response time performance of the invention. Exposure of the prototype GSD to individual protons of approximately 100 MeV, well within the energy range used for proton beam therapy, resulted in signals of duration less than 50 nanoseconds for most registered events. At longer scan times, no after-pulses were observed for several microseconds after the initial event. Even if there are slower (on microsecond or millisecond scale) components of gas scintillation after detecting a proton, their contribution is negligibly small. The GSD time response illustrated in FIGS. 5 and 6 is thus very well suited to fast dosimetry.

Figure 8:
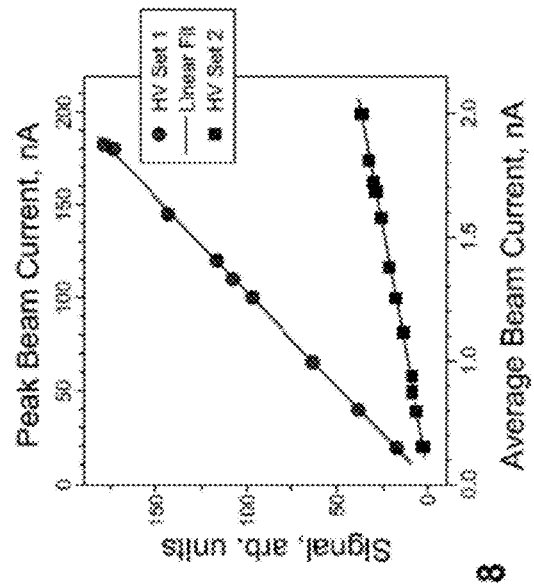
FIG. 8 is a graphical illustration of measured output signals as a function of incident pulsed proton beam current in a xenon-filled gas scintillation detector, according to an embodiment of the invention.
Figure 7:
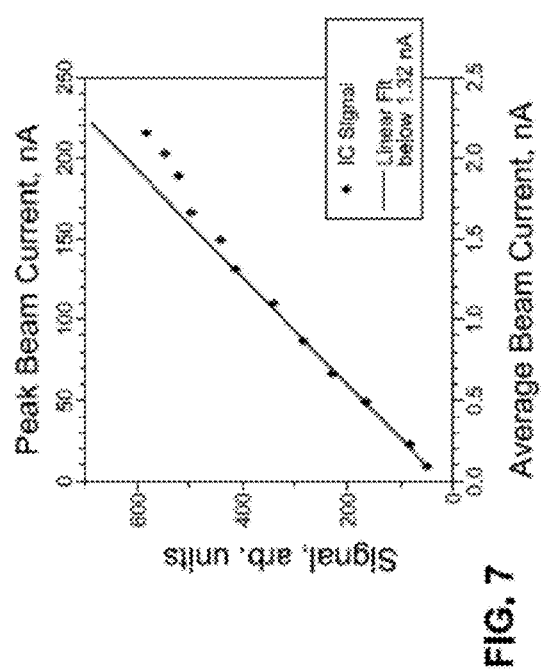
FIG. 7 is a graphical illustration of a measured output signal as a function of incident pulsed proton beam current in a conventional air-filled ionization chamber.

FIGS. 7 and 8 compare the linearity of the measured output signal as a function of incident pulsed proton beam current for (a) an air-filled parallel-plate ionization chamber (FIG. 7) and (b) a prototype xenon-filled GSD (FIG. 8) (at two different PMT gain settings). In each figure, the average beam current is shown on the lower horizontal axis and the instantaneous current during beam pulses on the upper horizontal axis.

As shown in FIGS. 7 and 8, the in-beam dosimetry performance of the prototype GSD was tested and compared to that for a conventional air-filled ionization chamber currently used for ion beam dosimetry, utilizing a pulsed 205 MeV proton beam from the Indiana University Cyclotron. Beam pulses of 20-microsecond-width were delivered with a duty factor of 1%, implying that instantaneous proton currents exceeded the average current by a factor of 100, as will be typical of proton therapy treatments utilizing superconducting synchrocyclotron accelerators. The results in FIG. 7 for the air-filled ion chamber show clearly that the ionization chamber response deviates significantly from linearity at the highest beam currents used (still somewhat lower than the maximum currents anticipated in clinical treatments), while the results in FIG. 8 for the xenon-filled prototype GSD show that the prototype GSD response retained excellent linearity throughout the entire tested region.

Figure 9:
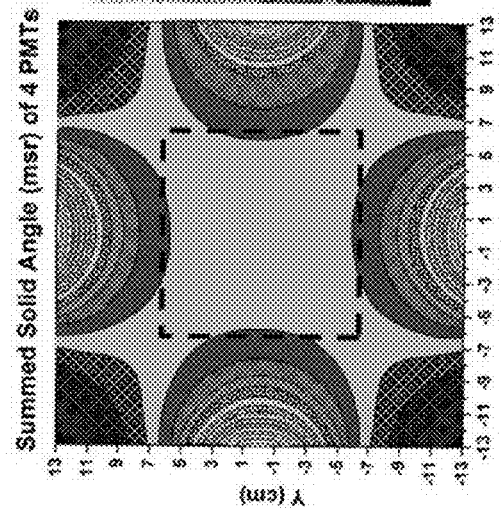
FIG. 9 is an illustration of a radiographic record of the net dose delivery in a proton spot beam scan for which the film was moved laterally back and forth through a water phantom.

FIG. 9 shows a record on radiographic film of the net dose delivery in a proton spot beam scan for which the film was moved laterally back and forth through a water phantom with a four-second period. The dose was delivered over a 10 cm×10 cm area in 43×43 voxels, with dose delivery to each voxel lasting for approximately six milliseconds. The vertical stripes 52 seen in the figure represent ~50% variations in dose resulting from the interplay of target and beam motion, illustrating potential complications introduced by organ motion for spot beam scanning treatments. When the film was held stationary, the same beam scan produced a uniform dose within a 10 cm×10 cm area. The proposed solution for such potential problems is to scan the beam over time intervals much shorter than patient breathing periods.

As can be seen from the measurements shown in FIG. 9 and from simulations, another technical challenge for spot beam scanning arises from complications due to organ motion within the patient. The interplay between the scanned beam and the target motion frequency may result in localized under-dosage in parts of the target volume and over-dosage in other parts. An illustration of this type of effect is seen clearly in the experimental results in FIG. 9. In these measurements, carried out at the clinical spot beam scanning treatment room at the ProCure (now Cadence Health) Proton Therapy Center in Warrenville, Ill., organ motion was simulated by use of an oscillating radiographic film to record the delivered dose. The film oscillation period was set to four seconds, an interval typical for patient breathing cycles. When the beam scan was performed at a rate typical of clinical spot beam scanning treatments, with each voxel irradiation taking approximately six milliseconds, the interplay of film and beam motion led to the ~50% variations in delivered dose as a function of position seen in FIG. 9.

In order to minimize effects such as those in FIG. 9 in clinical practice, it is important to execute each layer of a spot or raster beam scan over a time interval much shorter than a patient breathing period, preferably short enough (under 100 milliseconds) to allow multiple full scans (referred to as "repaints") over the same depth layer within a single breathing cycle, while the target tumor has not had a chance to migrate significantly. Clinical application of such fast beam scanning—even when it is carried out with accelerators that produce continuous, rather than pulsed, beams—demands accurate dose monitoring as a function of beam transverse position with feedback capability on sub-millisecond time scales, to correct potential dose delivery problems and avoid potential overdosage that could harm a patient.

As we now proceed to illustrate, the dosimeter described herein is capable of providing the needed monitoring with the accuracy, linearity, uniformity, fast response time and 1-2 mm spatial resolution required for clinical applications, to verify that the beam is actually delivering the doses and moving across the tumor as planned. Meeting these performance requirements in a single detector will provide a more cost-effective solution than alternatives that would use different detectors for absolute dose monitoring and for transverse beam position monitoring.

Figure 10:
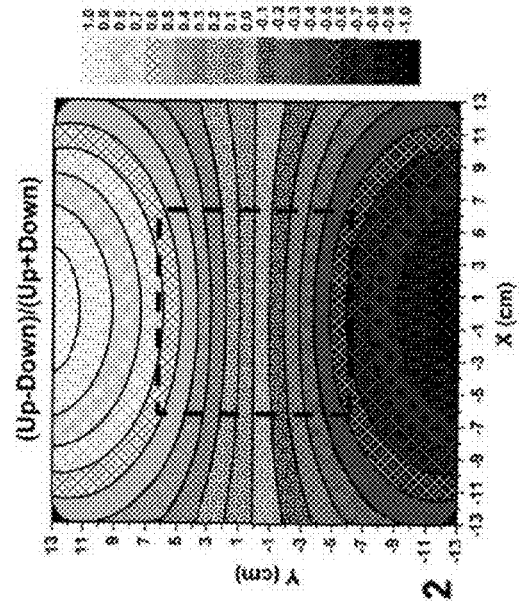
FIG. 10 is a graphical illustration of simulation results for contours of constant overall light collection efficiency versus lateral beam centroid position in a gas scintillation detector, constructed in accordance with an embodiment of the invention.

FIG. 10 shows simulation results for contours of constant overall light collection efficiency vs. lateral beam centroid position in a GSD of 18 cm radius, with non-reflective cylinder walls, read out by 4 PMTs of 25-mm diameter, each located at 90-degree intervals in azimuthal angle. The change between neighboring contour levels corresponds to a change in summed solid angle of the 4 PMTs of 10 millisteradians, or about 15% of the central light collection efficiency. The super-imposed dashed square indicates the largest treatment irradiation field dimensions of clinical interest.

With respect to the simulation of FIG. 10, the simulations of light collection efficiency in a GSD with readout by four PMTs demonstrate that it is possible to attain the desired level of spatial uniformity of the detector's response to radiation dose over an area of clinical interest for ion beam therapy. The simulation results in FIG. 10 were obtained under the assumption that the inner walls of the GSD housing 14 and of the entrance and exit windows 16 are made non-reflective. This can be arranged as well for the quartz windows 18 by means of thin anti-reflection coatings optimized for the wavelengths of peak optical emission from the scintillating gas. Under this assumption, the efficiency for collecting light in each of the four PMTs is simply proportional to the solid angle presented by each PMT to photons generated along the beam path.

The simulation results in FIG. 10 represent the sum of the four solid angles as a function of the two-dimensional transverse position at which photons are generated in the gas. The summed solid angle is seen to increase rapidly as the beam approaches any of the individual PMT locations, and to fall rapidly in the corners, where there is limited line of sight to two of the four PMTs. However, the summed solid angle for light collection is nearly constant over a sizable central region of the detector. Specifically, for PMTs of 25 mm diameter mounted around the circumference of a cylinder of 18 cm radius, the summed solid angle is nearly constant over a central square of 12.5 cm side length (indicated by the dashed lines in FIG. 10), as needed for a GSD placed halfway between a scanning nozzle and the patient isocenter if the dose is to cover a maximal area of 25×25 $cm^2$ at the isocenter.

Figure 12:
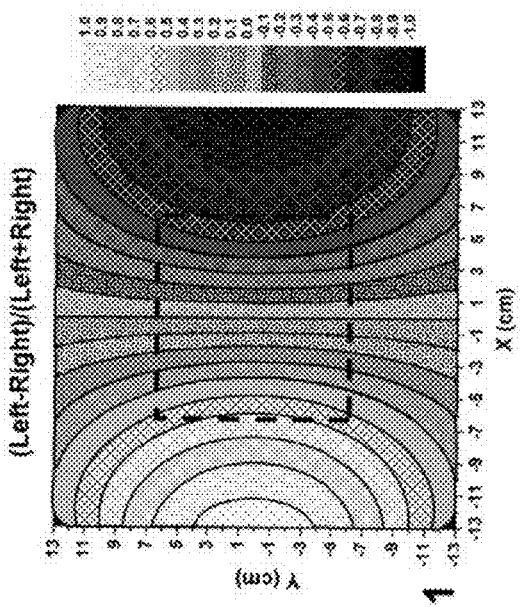
FIG. 12 is a graphical illustration of simulation results for contours of constant up-down signal asymmetries formed from the light collection efficiencies for each individual photo-detector in a xenon-filled gas scintillation detector, according to an embodiment of the invention.
Figure 11:
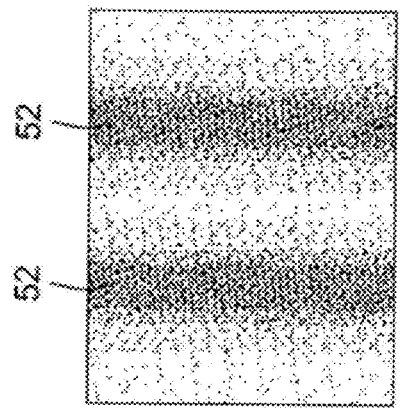
FIG. 11 is a graphical illustration of simulation results for contours of constant left-right signal asymmetries formed from the light collection efficiencies for each individual photo-detector in a xenon-filled gas scintillation detector, according to an embodiment of the invention.

FIGS. 11 and 12 show simulation results for contours of constant (a) left-right signal asymmetries (FIG. 11) and (b) up-down signal asymmetries (FIG. 12) formed from the light collection efficiencies for each individual PMT of the same detector configuration considered in FIG. 10. In both FIGS. 11 and 12, the simulated asymmetry changes typically by 0.1 for a beam movement of 10 mm. The superimposed dashed squares indicate the largest treatment irradiation field dimensions of clinical interest.

As shown, in FIGS. 11 and 12, the same simulations as in FIG. 10 reveal that it is possible to extract very good information on the beam location by forming asymmetries between pairs of photo-detectors that are diametrically opposed. Specifically, FIGS. 11 and 12 display the difference divided by the sum of the left and right PMT solid angles in FIG. 11 and of the up and down PMT solid angles in FIG. 12, each as a function of the two-dimensional transverse location at which photons are generated. The simulations in FIGS. 11 and 12 are for the same GSD geometry considered in FIG. 10, with the PMTs mounted at 18 cm radius. The contours in FIGS. 11 and 12 reveal that in the central region of interest (indicated by dashed squares), the left-right asymmetry varies linearly with horizontal position at which photons are generated, and that the up-down asymmetry varies linearly with vertical position, in each case changing by 10% per 10 mm shift in position of the photon origination points. These simulation results are quite consistent with the observed position-dependence of left-right differences for a tubular high-pressure xenon scintillation counter recently developed for gamma-ray spectroscopy, and exposed for tests to a movable collimated radioactive gamma-ray source.

The results in FIGS. 10, 11 and 12 are illustrative only. The actual position-dependent performance of the GSD may be optimized for different geometries, different numbers and locations of photo-detectors, different combinations of the photo-detector signals, and different inner wall surfaces. The present invention is intended to subsume all such alternative embodiments that achieve the same basic functionality via different choices of geometry, photo-detector layouts and algorithms for combining their signals, and materials and surface treatments.

In a spot or raster beam scan, the ion beam will, of course, have a transverse intensity profile. However, the fact that the asymmetries in FIGS. 11 and 12 depend linearly on position ensures that their values, when averaged over the intensity profile of the beam, will be the same as if the beam had been all concentrated at its intensity-weighted centroid position. The results in FIGS. 11 and 12 thus indicate that the transverse beam centroid position can be obtained from the photo-detector signal asymmetries, with a resolution of about 1 mm in each transverse dimension if the asymmetries can be measured to a precision of 1%. In a typical spot beam scan, neighboring voxels are separated by about 5 mm, a shift that should then be easily verifiable from the measured photo-detector asymmetries.

In actual use, the signals used to determine absolute dose and beam position will be derived from the integrated and digitized output currents from the photo-detectors. The amplitudes of these signals then depend not only on the solid angle for light collection, but also on the quantum efficiency for converting photons to electrons and on the electron multiplication gain of each photo-detector 20. In practice, then, the voltages applied to the photo-detectors 20, hence their gains, will be adjusted before clinical usage to match the output signals of the photo-detectors 20 when the GSD is irradiated by a narrow test beam directed along its central axis. If this test beam has moderate intensity, it will furthermore allow calibration of the summed photo-detector signal against an independent ionization chamber exposed to the same beam. (FDA regulations typically require redundant dose monitoring with two independent dosimeters for radiation therapy). The availability of light-pulsers 22 to illuminate the GSD volume will then allow periodic checks of signal stability during dose measurements. Any hardware problem leading to an unanticipated sudden gain shift of one photo-detector during measurements would be detectable via correlated unphysical changes in the apparent extracted values for both dose and beam position.

The number of photons generated in the GSD within each beam pulse from a superconducting synchrocyclotron or alternative pulsed accelerator will be more than sufficient to provide the desired precision on both dose and beam position in a clinical setting. For example, a 200 MeV proton traversing a xenon-filled GSD of 5 cm thickness at atmospheric pressure will deposit about 70 kilo-electron volts in the gas, leading to scintillation emission of about 2000 VUV photons. The central summed solid angle values in FIG. 10 correspond to collecting 0.5% of the produced photons, or 2.5 photons on average per PMT. If the quartz window transmission and PMT response curve in the vacuum ultraviolet region of xenon scintillation light convert half of these photons to electrons, with a quantum efficiency of 30%, then each proton will give an average probability ~40% to produce a single photoelectron in each PMT.

Typical proton therapy treatments utilize average beam intensities corresponding to $10^9$-$10^{11}$ protons/second (0.16-16 nanoamperes). If the beam pulse rate is 1 kHz, then each pulse delivers $10^6$-$10^8$ protons, which would then generate somewhere between 400 thousand and 40 million photo-electrons in each PMT, providing a statistical precision better than 0.15% on the measurement of each integrated PMT signal and better than 0.11% on the left-right and up-down asymmetries. If the PMT gain is only $10^3$ (corresponding to the lower curve in FIG. 8) and the pulse width is 10 microseconds, this produces PMT output currents during the beam pulse between 6 and 600 microamperes. Thus, the noise-to-signal ratio in the PMT output signals will be less than 1% as long as the dark current and background current in each PMT remains below 60 nanoamperes, a level that is normally achievable.

Hence, GSD position measurements, in which the processor 28 (shown in FIG. 4) determines ion beam position with spatial resolution on the order of one millimeter should be achievable in a single beam pulse from a superconducting synchrocyclotron or alternative pulsed accelerator. With a non-pulsed ion beam, one would want to integrate the PMT currents over time intervals on the order of 100 microseconds to achieve similar spatial resolution. But even for the fastest continuous raster beam scans envisioned, the beam will only have moved a few millimeters in 100 microseconds, so that the GSD measurements will still provide an extremely useful monitor of correct operation of the scanning system 42 (shown in FIG. 2). These position measurements will, in turn, allow the processor 28 (shown in FIG. 4) to implement real-time corrections to the desired (better than 2%) precision for the ~10% variations seen in FIG. 10 in summed light collection efficiency near the outermost edges of the largest envisioned treatment field.

The advantages of the present invention include, without limitation: (1) the high degree of linearity of detector response with incident beam flux needed for accurate dose monitoring in intensity-modulated ion beam therapy treatments, especially with beams from superconducting synchrocyclotrons or alternative pulsed accelerators; (2) the rapid detector response time needed for feedback on delivered dose to a given voxel, in order to halt or adjust, in real-time, the spot or raster beam scanning plan for subsequent voxel doses to ensure uniform tumor irradiation; (3) the capability to measure beam position with sufficient spatial resolution on a pulse-by-pulse basis for verification that the dose is being delivered to the intended voxel and that the beam moves by the intended amount from voxel to voxel; (4) the use of cost-effective components in a single detector meeting the above requirements, which will make the invention economically competitive with alternatives that provide significantly poorer performance.

In broad embodiment, the present invention is a fast in-beam, position-sensitive, absolute dose monitor for ion beam therapy, based on the detection of prompt primary scintillation light from a moderate-pressure gas volume traversed by the beam.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A radiation detector for absolute monitoring of radiation doses delivered by an ion beam comprising:
   a gas-tight housing with windows in the beam path;
   a gaseous medium within the housing, wherein scintillation light is emitted by the gaseous medium after it is traversed by the ion beam;
   one or more photo-detectors located within or around the gas-tight housing, the one or more photo-detectors configured to convert collected scintillation light into electric current;
   further comprising a processor configured to generate a digitized electronic signal whose magnitude is proportional to the total amount of light collected by the one or more photo-detectors;
   wherein the ion beam generates output data from the processor, the output data being indicative of a dose delivered by the ion beam to which the radiation detector was exposed, the output data being accurate to within 2% of the actual dose.

2. The radiation detector of claim 1, wherein the dose measurement accuracy of 2% is maintained over a full lateral extent of ion beam motion in two dimensions.

3. The radiation detector of claim 1, wherein the output data generated by the processor comprises an electronic signal whose magnitude is directly proportional to the dose delivered by the ion beam.

4. The radiation detector of claim 3, wherein the proportionality of the output data to the dose is maintained when the dose is delivered within ion beam pulses of one microsecond duration at instantaneous beam currents of up to 10 microamperes.

5. The radiation detector of claim 1, wherein the processor allows archiving of the digitized signals from each of the one or more photo-detectors on a beam-pulse-by-beam-pulse basis, or on a sampling-interval-by-sampling-interval basis, to provide a complete record of the dose delivered.

6. The radiation detector of claim 5, wherein the processor allows archiving of the digitized signals from each of the one or more photo-detectors to provide a complete record of the position at which the dose was delivered in each beam pulse or each sampling interval.

7. The radiation detector of claim 1, further comprising readout electronics coupled to the photo-detectors and to the processor and configured to integrate over time and digitize the electric current output by the one or more photo-detectors.

8. The radiation detector of claim 7, wherein the readout electronics are configured to be triggered by external electronic input signals to integrate photo-detector output electric currents only during time intervals when the ion beam is incident on the detector.

9. The radiation detector of claim 1, further comprising a photo-detector base for each of the one or more photo-detectors, wherein the photo-detector base couples its respective photo-detector to the readout electronics.

10. The radiation detector of claim 1, wherein the gas tight housing includes ion beam entry and exit windows sized to accommodate the movement of the ion beam in two dimensions.

11. The radiation detector of claim 1, wherein the one or more photo-detectors comprise one or more photomultiplier tubes, or one or more avalanche photodiodes.

12. The radiation detector of claim 1, wherein the one or more photo-detectors comprise a plurality of optical fibers or strip light guides to transport light to at least one multi-channel photo-detector.

13. The radiation detector of claim 1, wherein the at least one multi-channel photo-detector comprises at least one multi-anode photomultiplier tube.

14. The radiation detector of claim 1, further comprising wavelength-shifting optical fibers that shift the light emitted by the gaseous medium to improve overlap with a spectral response of the one or more photo-detectors.

15. The radiation detector of claim 1, wherein the gaseous medium comprises one of xenon and a mixture 95% argon with 5% carbon tetrafluoride.

16. The radiation detector of claim 1, wherein the gaseous medium is maintained at a pressure of approximately one atmosphere.

17. The radiation detector of claim 1, wherein the entire detector is mounted to a rotatable beam gantry, without interfering with a dose delivery apparatus or patient tables.

18. The radiation detector of claim 1, further comprising a quartz window to optically couple the gaseous medium and the one or more photo-detectors.

19. The radiation detector of claim 18, wherein the quartz window has an anti-reflection coating optimized for wavelengths of peak optical emission from the gaseous medium.

20. A radiation detector for absolute monitoring of radiation doses delivered by an ion beam comprising:
   a gas-tight housing with windows in the beam path;
   a gaseous medium within the housing, wherein scintillation light is emitted by the gaseous medium after it is traversed by the ion beam;
   one or more photo-detectors located within or around the gas-tight housing, the one or more photo-detectors configured to convert collected scintillation light into electric current;
   further comprising a processor configured to generate a digitized electronic signal whose magnitude is proportional to the total amount of light collected by the one or more photo-detectors;

wherein the output data of said processor are available on sub-millisecond time scales, the output data providing feedback for real-time adjustment of ion beam intensity for subsequent steps in dose delivery.

21. A radiation detector for absolute monitoring of radiation doses delivered by an ion beam comprising:
a gas-tight housing with windows in the beam path;
a gaseous medium within the housing, wherein scintillation light is emitted by the gaseous medium after it is traversed by the ion beam;
one or more photo-detectors located within or around the gas-tight housing, the one or more photo-detectors configured to convert collected scintillation light into electric current;
further comprising a processor configured to generate a digitized electronic signal whose magnitude is proportional to the total amount of light collected by the one or more photo-detectors; and
a plurality of photo-detectors located within or around the gas-tight housing, wherein the processor determines a difference between signals from oppositely-situated photo-detectors of the plurality of photo-detectors, divided by the sum of said signals, to provide output data sensitive to a distance of the ion beam from each of the oppositely-situated photo-detectors.

22. The radiation detector of claim 21, wherein the processor is configured to determine ion beam position with spatial resolution sufficient to detect beam motion from one beam pulse to the next.

23. The radiation detector of claim 22, wherein the gas-tight housing supports two or more pairs of oppositely-situated photo-detectors, wherein the processor is configured to determine two-dimensional movement of the ion beam from one beam pulse to the next.

24. The radiation detector of claim 22, wherein the processor is configured to determine ion beam position with spatial resolution of less than two millimeters in each of two dimensions.

25. The radiation detector of claim 24, wherein the spatial resolution of two millimeters is maintained over the full lateral extent of ion beam motion in two dimensions.

26. The radiation detector of claim 24, wherein the ion beam generates output data from the processor, the output data being indicative of a dose delivered by the ion beam to which the radiation detector was exposed, the output data being accurate to within 2% of the actual dose, and wherein the 2% dose accuracy and the two millimeter spatial resolution can be maintained for individual beam pulses under operating conditions in clinical applications of ion beam therapy delivery by pencil-beam scanning techniques.

27. A radiation detector for absolute monitoring of radiation doses delivered by an ion beam comprising:
a gas-tight housing with windows in the beam path;
a gaseous medium within the housing, wherein scintillation light is emitted by the gaseous medium after it is traversed by the ion beam;
one or more photo-detectors located within or around the gas-tight housing, the one or more photo-detectors configured to convert collected scintillation light into electric current;
wherein the beam entry and exit window materials and thicknesses are configured to withstand a pressure differential of more than one atmosphere, and configured to introduce less than 2 milliradians root-mean-square angular spread in a 200 MeV proton beam.

28. A radiation detector for absolute monitoring of radiation doses delivered by an ion beam comprising:
a gas-tight housing with windows in the beam path;
a gaseous medium within the housing, wherein scintillation light is emitted by the gaseous medium after it is traversed by the ion beam;
one or more photo-detectors located within or around the gas-tight housing, the one or more photo-detectors configured to convert collected scintillation light into electric current; and
one or more light-pulsers, each of which emits light at wavelengths within the spectral response region of the one or more photo-detectors, and are triggered by external electronic signals to provide periodic calibration of all photo-detector responses to reproducible amounts of light injected at known locations.

29. The radiation detector of claim 28, wherein the one or more light-pulsers comprise one or more light-emitting diodes.

30. The radiation detector of claim 28, wherein the one or more light-pulsers are embedded inside of the gas-tight housing.

31. A radiation detector for absolute monitoring of radiation doses delivered by an ion beam comprising:
a gas-tight housing with windows in the beam path;
a gaseous medium within the housing, wherein scintillation light is emitted by the gaseous medium after it is traversed by the ion beam;
one or more photo-detectors located within or around the gas-tight housing, the one or more photo-detectors configured to convert collected scintillation light into electric current;
wherein the scintillation light, emitted by the gaseous medium, has a duration of less than 100 nanoseconds.

* * * * *